United States Patent [19]

Paul et al.

[11] Patent Number: 4,746,755

[45] Date of Patent: May 24, 1988

[54] PREPARATION OF HYDRANTOIC ACIDS AND HYDANTOINS

[75] Inventors: Albertha M. Paul, Holliston; Harold H. Freedman, Newton Center, both of Mass.

[73] Assignee: The Dow Chemical Company, Midland, Mich.

[21] Appl. No.: 860,161

[22] Filed: May 6, 1986

[51] Int. Cl.$^4$ .............................................. C07C 99/00
[52] U.S. Cl. .................................... 562/450; 564/48; 544/386; 544/168
[58] Field of Search .......................... 562/450; 564/48; 544/386, 168

[56] References Cited

U.S. PATENT DOCUMENTS

| | | | |
|---|---|---|---|
| 3,020,145 | 2/1962 | Gobeil et al. | 71/2.6 |
| 3,676,456 | 7/1972 | Gruenfeld | 548/309 |
| 3,684,774 | 8/1972 | Merten et al. | 562/439 |
| 3,798,233 | 3/1974 | Akiba | 562/439 |
| 3,846,441 | 11/1974 | Mime et al. | 71/92 |
| 4,076,941 | 2/1978 | Sauli | 548/312 |
| 4,093,444 | 6/1978 | Clapot et al. | 71/92 |
| 4,230,716 | 10/1980 | Jamieson et al. | 562/439 |
| 4,241,074 | 2/1980 | Cassidy | 548/309 |

FOREIGN PATENT DOCUMENTS 1067212 10/1959 Fed. Rep. of Germany ...... 562/450

OTHER PUBLICATIONS

Stoutland et al., J. Org. Chem., vol. 24, pp. 818-820, (1959).

*Primary Examiner*—James H. Reamer
*Attorney, Agent, or Firm*—Charles J. Enright

[57] ABSTRACT

The specification discloses reacting a water soluble amino compound with a highly water reactive isocyanate by dissolving the isocyanate in a solvent, such as ethyl acetate, which is water insoluble to slightly water soluble and which has a degree of electrophilicity so as to attract the amino constituent of the amino compound. The two solutions are rapidly mixed together, affording superior yields of product.

9 Claims, No Drawings

PREPARATION OF HYDRANTOIC ACIDS AND HYDANTOINS

BACKGROUND OF THE INVENTION

The present invention relates to a method for reacting water soluble (organic solvent insoluble) amino compounds with isocyanates which are highly reactive with water. Examples of such reactions include the preparation of hydantoins and/or hydantoic acid by reacting amino acids or peptides with reactive isocyanates.

The problem with such reactions is that the isocyanate is hydrolyzed by water to form an undesired urea compound. This undesirable reaction competes with the desired reaction between the isocyanate and the amino compound.

The primary technique used by artisans to obviate this problem is to add the isocyanate very slowly to an aqueous solution of the alkali salt of the amino acid with stirring. The reaction is typically conducted at about 50° C. over a two hour period.

U.S. Pat. No. 3,020,145 teaches adding the amino solution slowly to a solution of isocyanate in a water soluble inert solvent, as for example acetone. U.S. Pat. Nos. 4,230,716, 4,093,444 and 3,798,233 have similar disclosures. All of these procedures are relatively slow.

SUMMARY OF THE INVENTION

In the present invention, the reaction between the isocyanate and the amino compound is carried on very rapidly. The highly water reactive isocyanate is dissolved in an organic solvent which is insoluble to slightly soluble in water and has a degree of electrophilicity sufficient to attract the amino constituent of the amino compound. The amino compound is in turn dissolved in water. The two solutions are rapidly mixed together to effect a biphasic reaction therebetween. The reaction is essentially instantaneous and provides very high yields.

DESCRIPTION OF THE PREFERRED EMBODIMENT

In the preferred embodiment, the reaction of the isocyanate and the amino compound is carried out in a basic medium to form the sodium salt of the hydantoic acid. The reaction product is acidified to form the hydantoic acid and/or the hydantoin. The reaction is illustrated below for phenyl isocyanate and sodium glycinate:

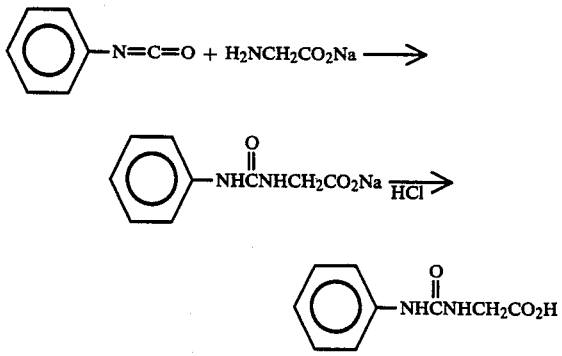

The organic solvent selected for the isocyanate must of course be one in which the isocyanate is soluble. It must be insoluble to only slightly soluble in water. It must have a degree of electrophilicity sufficient to attract the amino constituent of the amino compound.

Ethyl acetate has been found to be an excellent organic solvent for this reaction. It has a solubility in water of 8.6 grams per 100 milliliters. It has the sufficient degree of electrophilicity at its double bonded oxygen atom. While the precise mechanism for the operability of the reaction is not known, it is theorized that the amino component is attracted to the ethyl acetate at the interface between the water and the ethyl acetate. This forms a shield which prevents the isocyanate from reacting with the water and instead allows the reaction to proceed preferentially with the amino component. This is illustrated below:

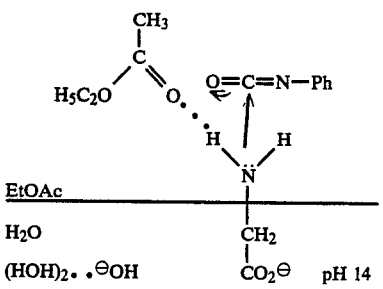

In contrast, solvents such as ether, methylene chloride and toluene are not operable in the present invention. Ether has a solubility in water which is comparable to ethyl acetate. However, it lacks sufficient electrophilicity. Methylene chloride and toluene are similarly defective.

Solvents which are soluble in water are not operable because they fail to provide any protection for the isocyanate vis-a-vis the water.

The amino compound must be maintained in a basic solution. In an acid solution, the nucleophilicity of the amino component is diminished and mixing the two solutions yields only the diurea compound formed by hydrolysis of the isocyanate. Most preferably, the amino compound solution in water is maintained at a pH of between 10 and 14.

The isocyanate and amino compound are reacted at a 1:1 molar ratio. Neither an excess of isocyanate nor an excess of the amino compound yields any significant improvement in results.

Both the organic solvent and the water should be present in molar excess with respect to their dissolved compounds. Preferably, the ethyl acetate is present in a 16 fold molar excess to the isocyanate while the water is present in an 80 to 100 fold molar excess of the amino compound. The use of too little ethyl acetate vis-a-vis the isocyanate results in a lower yield of product. Use of greater than 16 fold molar excess gives no advantages. Similarly, the use of too little water results in lower yields. Sufficient water must be used to totally dissolve the amino compound. Use of water in excess of the 80 to 100 fold molar ratio is desirable only to the extent that it may in some cases be necessary to totally dissolve the amino compound.

The two solutions are mixed vigorously. A magnetic stirrer operating at 200 rpm or greater is usually sufficient to give the desired degree of mixing of the two phases. Preferably, the aqueous solution of amino compound is stirred and the ethyl acetate solution of isocyanate is added essentially all at once. The stirring is continued for five to 10 minutes, at which time the layers are separated and the aqueous layer made acidic with concentrated hydrochloric acid. The resulting precipitate is filtered and dried.

Longer times may be necessary for some reactions. For primary amino compounds, the reaction take place very rapidly, as for example within a matter of 10 seconds for laboratory quantities. The reaction takes longer for secondary amino compounds, as for example from 10 to 30 minutes.

The reaction is carried out at atmospheric pressure and no pressure is generated during the course of the reaction. Conducting the reaction at between 0° and 50° C. does not affect product yield. The reaction is of course slower at lower temperatures. One could conduct the reaction at temperatures higher than 50° C., but it is not usually necessary to do so.

The method of the present invention is strikingly successful in the reaction of primary amino compounds. It is operable with secondary amino compounds. As the amino compounds become less nucleophilic, however, the effectiveness of the present invention diminishes. In the case of some reactants, as for example piperidine, the conventional technique of slowly adding the isocyanate to an aqueous alkaline solution of the amino compound may actually work better.

Similarly, the method of the present invention is especially effective when aryl isocyanates are used in the reaction. These are of course especially reactive with water. The invention does not work as well with less reactive isocyanates, as for example isothiocyanates and short chained (see less than $C_6$) alkyl isocyanates. The shielding caused by the ethyl acetate makes the reaction unnecessarily slower. Shielding is unnecessary in that hydrolysis is slower for these less reactive isocyanates, making the amino reaction relatively more competitive.

EXAMPLES

Table 1: Varying Temperature And Mixing Rate In The Present Invention And In The Prior Art Method In the eight examples contained in Table 1, the method of the present invention (methods b and d) was compared to the prior art aqueous alkaline method (a and c) while varying reaction temperature and the degree of stirring. The reactants were phenyl isocyanate and sodium glycinate.

In method a, 0.05 moles of sodium glycinate was dissolved in 150 cc of water and maintained at a pH of 10-14. This solution was stirred at 200 rpm with a magnetic stirrer. 0.05 moles phenyl isocyanate was added very slowly over a period of about 30 minutes. The stirring was continued for two hours.

In method b, 0.05 moles of phenyl isocyanate was dissolved in 80 cc of ethyl acetate. 0.05 moles of sodium glycinate was dissolved in 150 cc of water. The pH was maintained at between 10 and 14. The aqueous alkaline solution was stirred at 200 rpm with a magnetic stirrer and the ethyl acetate solution of phenyl isocyanate was added all at once.

Method c was the same as method a except that a homogenizer was used to effect very rapid stirring, e.g., 45,000 rpm.

Method d was the same as method b, except that again, the homogenizer was used to effect very rapid stirring.

In methods b and d, the aqueous and organic solvent phases were separated after the reaction was completed. The aqueous phase was acidified with concentrated hydrochloric acid. The same acidifying step was used in methods a and c. The resulting precipitate was filtered and vacuum dried at 60° C.

The results of these experiments are reported in Table 1 below:

TABLE 1
REACTION OF PhNCO AND SODIUM GLYCINATE

| Run No. | Method | Temp (°C.) | Time (h) | Yield % (Hydantoic Acid) | M.P. °C. |
|---|---|---|---|---|---|
| I | a | 50 | 2 | 74 | 194.6 |
| II | b | 50 | 2 | 93 | 195 |
| III | a | Rm | 16 | 50 | 194 |
| IV | b | Rm | 16 | 97 | 195 |
| V | b | Rm | 2 | 93 | 195 |
| VI | c | Rm | 0.08 | 72 | 194 |
| VII | d | Rm | 0.08 | 97 | 194 |
| VIII | b | 0–5 | 0.25 | 93 | 195 | a = Aqueous Alkaline Condition
b = Aqueous Alkaline Condition/ethyl acetate
c = Aqueous Alkaline Condition/homogenizer
d = Aqueous Alkaline Condition/ethyl acetate/homogenizer In all cases, the method of the present invention resulted in yields in excess of 90%, regardless of the reaction temperature or the rate of stirring. In contrast, the prior art methods yielded 74%, 50% and 72% respectively.

Table 2: Comparison Of Ethyl Acetate To Other Organic Solvents

In the examples of Table 2, method b described above was used in all cases. The reactions were conducted at room temperature. Various organic solvents were substituted for ethyl acetate.

TABLE 2
COMPARISON OF EtOAc TO OTHER ORGANIC SOLVENTS $$PhNCO + NH_2CH_2CO_2Na \longrightarrow \underset{H^+}{\longrightarrow} PhNHCONHCH_2CO_2H$$

| H₂O/Organic Solvent | Yield (%) (Isolated) |
|---|---|
| Ethyl acetate | 98 |
| Ether | 76 |
| $CH_2Cl_2$ | 50 |
| Toluene | 55 |
| Ethanol | 38 |
| DMF (dimethyl formamide) | 31 |

The product yield was 98% when ethyl acetate was used, whereas the best alternative solvent, ether, provided a yield of only 76%. The ethanol and DMF were of course soluble in water and hence provided the lowest product yield.

Table 3: Effect Of pH On The Reaction

In the examples reported in Table 3, method b was used, except that the pH was varied. At a pH of 6 or below, the only product obtained was the undesirable diurea formed by the hydrolysis of the isocyanate. On the other hand at pH's of 10 to 14, the desired hydantoic salt, and then hydantoic acid and/or hydantoin as a result of acidification thereof, was obtained in 98% yields. These results are illustrated in Table 3 below:

TABLE 3

EFFECT OF pH ON THE REACTION

PhNCO +

H$_2$NCH$_2$CO$_2$Na$\longrightarrow$ $\longrightarrow$ PhNHCONHCH$_2$CO$_2$H + PhNH$_2$CO 1. EtOAc/H$_2$O               (A)          (B)
2. H$^+$

| pH Reaction Condition | YIELDS (%) isolated | |
|---|---|---|
| | A | B |
| 1. pH 4 (adjusted w HCl) [Cl$^\ominus$NH$_3$CH$_2$CO$_2$H] | 0 | 100 |
| 2. pH 6 (no NaOH) [H$_3^\oplus$NCH$_2$CO$_2^\ominus$] | 0 | 100 |
| 3. pH 10-14 (normal conditions) [NH$_2$CH$_2$CO$_2$Na] | 98 | $\leq 2$ |

Table 4: Effect Of Level Of Water And Solvent On The Reaction

The examples reported in Table 4 were conducted in accordance with method b above, except that the quantities of ethyl acetate and water were varied as indicated. It can be seen that either too little water (examples 1 and 2) or too little ethyl acetate (example 3) failed to give the high yields of hydantoic acid/hydantoin which are achieved by employing a molar excess of water and ethyl acetate.

TABLE 4

EFFECT OF LEVEL OF H$_2$O ON THE REACTION

PhNCO +

NH$_2$CH$_2$CO$_2$Na$\longrightarrow$ $\longrightarrow$ PhNHCONHCH$_2$CO$_2$H +

(PhNH)$_2$—C=O

EtOAc/H$_2$O    H$^+$

A    B                C         D

REACTION CONDITIONS

| Run No. | H$_2$O (mol) | EtOAc (mol) | A (mol) | B (mol) | YIELDS (%) | | |
|---|---|---|---|---|---|---|---|
| | | | | | C | D | A |
| 1. | 0 | 0.82 (80 cc) | 0.05 | 0.05 | 74 | $\leq 1$ | 25 |
| 2. | 0.05 | 0.82 | 0.05 | 0.05 | 83 | $\leq 1$ | 15 |
| 3. | 8.3 (150 cc) | 0.05 | 0.05 | 0.05 | 77 | 20 | — |
| 4. | 8.3 | 0.82 | 0.05 | 0.05 | 98 | $\leq 1$ | — |

Table 5: Reactions Involving Other Amino Compounds

In the examples shown in Table 5, other amino compounds were reacted with phenyl isocyanate in accordance with methods a and b above. As can be seen by reference to Table 5, the yields as a result of utilizing the present invention (method b) were consistently higher than the yields obtained using the prior art, slow addition technique.

TABLE 5

| STARTING MATERIAL | PRODUCTS | | YIELD (%) | |
|---|---|---|---|---|
| | hyd. | acid hyd. | method a | method b |
| 1. Sarcosine | 3 | 4 | 57 | 67 |
| 2. Iminodiacetic acid | 0 | 5 | 67 | 75 |
| 3. Glycineglycine | 2 | 0 | 30 | 85 |
| 4. Glutamic acid | 0 | 6 | 1 | 40 |
| 5. Ethanolamine | 7 | 0 | 75 | 98 |
| 6. Piperazine | 8 | 0 | 71 | 75 |
| 7. Morpholine | 9 | 0 | 72 | 93 | a aqueous alkaline condition according to literature
b aqueous condition with ethyl acetate as co-solvent In the sarcosine reaction, the yield reflects the combination of the hydantoic acid and hydantoin. In the practice of the prior art method, the ratio of hydantoic acid to hydantoin was 2.5:1. In practicing the present invention, the ratio of hydantoic acid to hydantoin was 3.5:1.

CONCLUSION

By dissolving the isocyanate in an organic solvent which is insoluble to slightly soluble in water and has a degree of electrophilicity sufficient to attract the amino constituent of an amino compound, one can rapidly react an isocyanate with a water soluble amino compound and obtain quantitative yields of a hydantoin and/or hydantoic acid. The aqueous amino compound solution should be basic and should be vigorously stirred during addition of the isocyanate solution. The resulting hydantoic acid salt is then acidified to yield the hydantoic acid and/or hydantoin.

Of course, it is understood that the above is merely a preferred embodiment of the invention and that various changes and alterations can be made without departing from the spirit and broader aspects thereof as set forth in the appended claims.

The embodiments of the invention in which an exclusive property or privilege is claimed are defined as follows:

1. A method for reacting water soluble, organic solvent insoluble amino compounds with highly water reactive isocyanates comprising:
    dissolving said isocyanate in an organic solvent which is insoluble to slightly soluble in water and has a degree of electrophilicity suficient to attract the amino constituent of said amino compound;
    dissolving said amino compound in water;
    rapidly mixing the resulting solutions together, wherein said organic solvent is ethyl acetate.

2. The method of claim 1 in which a basic pH is maintained in said aqueous solution.

3. The method of claim 2 in which the pH of said aqueous solution is maintained at between about 10 and 14.

4. The method of claim 3 in which said amino compound is dissolved in a molar excess of water of from about 80 to 100:1.

5. The method of claim 4 in which said isocyanate is dissolved in a molar excess of said organic solvent of about 16:1.

6. The method of claim 5 in which said isocyanate is an aromatic isocyanate.

7. The method of claim 6 in which said amino compound is a primary amino compound.

8. The method of claim 2 in which said isocyanate is an aromatic isocyanate.

9. The method of claim 8 in which said amino compound is a primary amino compound.

* * * * *